United States Patent [19]

Maeda et al.

[11] 4,442,093

[45] Apr. 10, 1984

[54] METHOD FOR ADMINISTERING 24,25-DIHYDROXYCHOLECALCIFEROL TO PERSONS SUFFERING FROM HYPERCALCEMIA

[75] Inventors: Yuji Maeda, Matsudo; Takayoshi Fujii, Tokyo; Yasuhiko Kobayashi, Tokyo; Kenichi Saito, Tokyo; Tadaaki Kato, Tokyo; Chikao Yoshikumi, Kunitachi, all of Japan

[73] Assignee: Kureha Kagaku Kogyo Kabushiki Kaisha, Tokyo, Japan

[21] Appl. No.: 374,702

[22] Filed: May 4, 1982

[30] Foreign Application Priority Data

| May 15, 1981 | [JP] | Japan | 56-73264 |
| Dec. 9, 1981 | [JP] | Japan | 56-198015 |
| Dec. 9, 1981 | [JP] | Japan | 56-198016 |
| Feb. 8, 1982 | [JP] | Japan | 57-18600 |
| Apr. 15, 1982 | [JP] | Japan | 54-62688 |
| Apr. 20, 1982 | [JP] | Japan | 54-65869 |
| Apr. 27, 1982 | [JP] | Japan | 54-70682 |

[51] Int. Cl.$^3$ .............................................. A61K 31/59
[52] U.S. Cl. ..................................................... 424/236
[58] Field of Search ....................... 260/397.2; 424/236

[56] References Cited

U.S. PATENT DOCUMENTS

| 3,715,374 | 2/1973 | De Luca | 260/397.45 |
| 3,994,878 | 11/1976 | Partridge et al. | 260/397.2 |
| 4,364,941 | 12/1982 | Kiyoki et al. | 424/236 |

*Primary Examiner*—Elbert L. Roberts
*Attorney, Agent, or Firm*—Wegner & Bretschneider

[57] ABSTRACT

Pharmaceutical composition in dosage unit form, comprising a therapeutically effective amount of 24,25-dihydroxycholecalciferol and a pharmaceutically acceptable carrier. The compound of 24,25-dihydroxycholecalciferol has anti-hypercalcemic activity, anti-ulcer activity, activity of preventing reduction of immunity, activity of controlling magnesium-metabolism, anti-hyperphosphatemic activity, activity of controlling blood sugar level and anti-tumor activity.

4 Claims, No Drawings

METHOD FOR ADMINISTERING 24,25-DIHYDROXYCHOLECALCIFEROL TO PERSONS SUFFERING FROM HYPERCALCEMIA

BACKGROUND AND DETAILED DESCRIPTION OF THE INVENTION

The present invention relates to a pharmaceutical composition containing 24,25-dihydroxycholecalciferol (hereinafter referred to as 24,25-$(OH)_2$-$D_3$ or the present compound) as an active ingredient.

The present inventors have found that 24,25-$(OH)_2$-$D_3$ has anti-hypercalcemic activity, anti-ulcer activity, activity of preventing reduction of immunity, activity of controlling magnesium-metabolism, anti-hyperphosphatemic activity, activity of controlling blood sugar level and anti-tumour activity.

It is an object of the present invention to provide a pharmaceutical composition in dosage unit form, comprising a therapeutically effective amount of 24,25-$(OH)_2$-$D_3$ and a pharmaceutically acceptable carrier. Another object is to provide a method for treating hypercalcemia, ulcer, reduced immune function, metabolic abnormality on magnesium, hyperphosphatemia, abnormality on blood sugar such as hyperglycemia or tumour, which comprises administering a therapeutically effective amount of 24,25-$(OH)_2$-$D_3$ to a human or an animal suffering from the above-mentioned disease. Further object is to provide a process for preparing the pharmaceutical composition. Still other objects will appear hereinafter.

The pharmaceutical activities of the present compound will be described in detail as follows:

Hypercalcemia is a disease of a person whose calcium level in serum has been abnormally raised, and frequently occurs in complication with a disease such as malignant tumour, intoxication due to Vitamin D, sarcoidosis and hyper-parathyroidism.

As a pharmaceutical for treating hypercalcemia, calcintonin has been administered, however, calcitonin which is a peptide hormones is not persistent within the patient's body to which it has been administered and accordingly, there is a problem of durability of its effect. In addition, since calcitonin cannot be orally administered, it must be parenterally administered, for instance, by intramuscular injection, and accordingly, calcitonin has a demerit of being accompanied by the patient's pain. Furthermore, it is pointed out that the administration of calcitonin of non-human origin is accompanied by the reduced effect and anaphylactic shock due to the production of the antibody.

In these situations, the development of an orally administable anti-hypercalcemic agent which is excellently long-lasting in its pharmacological effect has been eagerly awaited.

Concerning the effect of 24,25-$(OH)_2$-$D_3$ on calcium in serum, the following reports have been known:

(a) Norman, A. W., J. M. Canterbury, Journal Clin. Invest., 78, 1375-1383, 1978:

It is reported that on the continuous injection of 24,25-$(OH)_2$-$D_3$ for 20 min into the healthy dog's thyroid artery, the level of calcium in the dog's serum showed a temporary reduction, however, the level returned to the normal value immediately thereafter. For reference, different from the ordinary administration such as oral-, subcutaneous-, intraperitoneal- and intravenous administration, the continuous injection of an agent into the thyroid artery is a specific method of administration.

(b) Canterbury, J. M., Clin. Res., 26, N1, PA 31, 1978:

It is reported that the administration of 24,25-$(OH)_2$-$D_3$ to a dog suffering from hyper-parathyreosis by the thyroid arteral route did not change the dog's calcium level in serum.

(c) Norman, A. W., Brit. Med. J., 280 (No. 6212), 449-450, 1980:

It is reported that the oral administration of 250 micrograms of 24,25-$(OH)_2$-$D_3$ to a normal person did not cause the significant change of calcium level in his serum.

(d) Although the following reports concern the administration of 24,25-$(OH)_2$-$D_3$ to the patients suffering from hypocalcemia, non of them reported the case where the calcium level in the patient's serum showed a significant change by the administration:

Kanis, J. A., Brit. Med. J., (1978) 1382-1386;

Rasmussen, H., J. Clin. Endocrin. Metab., 46, 284-294 (1978);

Szymendera, J., Brit. Med. J. (Nov. 28) 1465-1466 (1978); and

Kanis, J. A., V-D Basic Research and Its Clinical Appl., (1979), 119-122.

As mentioned above, so far as the present inventors are informed of, there are no reported case where 24,25-$(OH)_2$-$D_3$ was administered to human patient of hypercalcemia or animals in the similar morbid state.

As a result of studying and examining the functions of substances present in human body, of which the safety has been confirmed, the present inventors have found that 24,25-$(OH)_2$-$D_3$ are effective in treating hypercalcemia, particularly in view of its long-lasting pharmacological effect and its possibility of being orally administered, and have arrived at the present invention.

Anti-ulcer activity of the present compound is described as follows:

Peptic ulcer is the ulcer formed on the weakened part of the mucous membrane of stomach or intestine as the damage of substance of the membraneous layer by the action of attacking factor such as hydrochloric acid and pepsin. Although the slight cases are curable by treatment with hospitalization for 3 to 4 months, in the severe cases, hemorrhage and perforation frequently occur and the morbid state becomes chronic.

As the cause of peptic ulcer, the autonomic imbalance and the abnormality of mucous blood flow by the physical and mental stress have been considered, however, since the internal organs themselves are under complicated control of neurohormone, it is practically impossible to elucidate simply to cause of peptic ulcer.

As the conventional anti-ulcer agent, sodium hydrogen carbonate, aluminum salts and magnesium salts have been used for a long time in the sense of neutralizing the acid as one of the attacking factors to the mucous membrane, however, these agents neutralize the acid only temporally to relieve the pain and have scarcely the healing effect on the ulcer.

Recently, anti-ulcer agents based on the presumed cause of ulcerous diseases such as the depressant of autonomic nerve system (so-called anti-choline agent), the reparative agent and the blood flow-improving agent have been numerously developed. However, they are not necessarily satisfactory from the viewpoints of effectiveness or side effects.

Since it takes a long period of time to carry out the treatment of the peptic ulcer, the administration of an anti-ulcer agent frequently extends over a long period of 100 to 150 days on the average, and accordingly, the high treating effect and particularly, the high safety are required to antipeptic ulcer agent.

The present inventors while taking the above-mentioned situation into account have examined the compounds which are endogenously present in a healthy human body, excellent in anti-peptic ulcer activity and pharmacologically quite safe, and as a result of the examination, they have found that 24,25-$(OH)_2$-$D_3$ is suitable for their purpose. Our present invention has been completed upon the finding.

The following description relates to the activity of the present compound in preventing the reduction of immunofunction:

Renal failure or uremia is one of the representative diseases which are progressive and bring about extensive reduction of immunity. According to the result of investigation in Japan, 38.3% of infectious cases has been recognized in acute renal failure and 19.2% of infectious cases has been recognized in chronic renal failure. Accordingly, there are many death cases due to infectious diseases, and according to the statistics of mortality on patients subjected to long term hemodialysis, 13.3% of death cases was due to infectious diseases. It is said that immunofunctional failure in renal failure appears as the cellular immunofunctional failure rather than the humoral one (refer to Clinical Immunology (Japan), 12(8), 607-614, 1980).

The infection in various renal diseases can be prevented by preventing or recovering the reduction of immunofunction.

After studying for finding the agent which prevents the reduction of immunofunction concerning renal diseases, the present inventors have found that 24,25-$(OH)_2$-$D_3$ is effective for that purpose, and have arrived at the present invention.

Since the cellular immunofunctional failure appears more remarkably than the humoral one in the renal diseases, the present inventors have examined mainly the effect of the present compound on the thymus which controls the cellular immunofunction. As the results of administration of the present compound to experimental animals, it is found that the present compound prevents the reduction of the following factors: the weight ratio of thymus to whole body, the number of thymocytes, the pattern of the size of thymic cells and blastoid-transformation of lymphocytes.

Namely, the present compound is useful as an agent for preventing the reduction of immunofunction in renal diseases for instance, chronic renal failure, uremia, and nephrotic syndrome.

In the next place, the activity of the present compound in controlling magnesium-metabolism will be explained as follows:

Magnesium stands fourth in cations within the body in abundance, and within cells magnesium stands next to potassium. Its abundance in extracellular fluid stands in the descending order of sodium, potassium, calcium and magnesium. Magnesium within the cells is in close connection to the activities of many enzymes, and magnesium in the extracellular fluid concerns the excitation of nerves and muscles. Moreover, magnesium is the essential element to the functions of a number of enzymes, for instance, those in glycolysis, and concentration of magnesium in serum is kept within a fixed range. One third of the magnesium in bone presents within the superficial layer of bone, particularly in the surface of hydroxyapatite to flow out of the osseous tissue for keeping the equilibrium with magnesium in serum.

The abnormality in magnesium metabolism has been observed in various morbid cases in spite of its equilibrium within the body (refer to Japanese J. Clin. Med., 38 (special spring number) 275-287, 1980).

Recently, studies on magnesium metabolism in the patients suffering from renal failure and receiving homodialysis have been carried out, and it is suggested that the serum level of magnesium is raised by actual hemodialysis and that there is a relationship between the serum level of magnesium and metastatic calcification.

Accordingly, it becomes possible to alleviate, prevent or improve various diseases by returning the abnormal magnesium metabolism to the normal one.

In consideration of the above-mentioned situation, development of an agent for normalizing the abnormalized magnesium metabolism has been demanded.

As a result of studying on the endogenous substances present within healthy human body, of which the safety has been confirmed, the present inventors have found that 24,25-$(OH)_2$-$D_3$ is able to control the metabolism of magnesium, and based on the finding, the present inventors have attained the present invention.

For reference, concerning the metabolism of magnesium, the following articles have been publicly reported:

(1) Proceeding of XVII KAWAGUCHI-KO Conference on the relationship between hormones and water or electrolytes, 155-167, 1981. Ed. ISIYAKU-Publishing Co. (Japan).

The present compound administered once to the rats subjected to thyroidectomy and parathyroidectomy did not affect the magnesium level in serum thereof and the magnesium clearance thereof.

(2) Pavlovitch, J. H., J. Clin, Invest., 68, 803-810 (1981).

The present compound preliminarily administered to the rats subjected to bilateral nephrectomy did not affect significantly the magnesium level in serum thereof.

The present inventors could not find any report which informs the beneficial effect of the present compound on the metabolism of magnesium.

It has been also known that there are no definite relationships between calcium and metabolism of magnesium (refer to Walsor, M. J., J. clin. Invest., 40, 723-730, 1961).

The agent for controlling metabolism of magnesium according to the present invention is the agent for restoring the abnormal state of concentration of magnesium within living body to the normal state and for preventing the abnormal change of the concentration of magnesium within living body.

The abnormality in magnesium metabolism has been observed in various diseases, for instance, renal diseases nerval diseases, diseases due to abnormal osseous metabolism, diseases on internal secretion, digestive troubles and diseases of circulatory system, and accordingly, the present compound makes it possible to alleviate, improve or prevent these diseases.

The anti-hyperphosphatemic activity of the present compound is described as follows:

Hyperphosphatemia has become an issue recently. It occurs mainly due to the reduction of excreting function (increase of reabsorption) in the kidneys in the morbid state such as that of chronic renal failure, hypoparathyroidism, acromegaly and acute disused-bone atrophy.

In the recent years, the number of patients receiving a long-term hemodialysis due to chronic renal failure goes on increasing and because their frequent development of a complication of symptoms such as metastatic calcification and metabolic acidosis due to their hyperphosphatemia, inorganic phosphate within their blood has been controlled by the increase in frequency of dialysis, the restriction of phosphorous in their diet and the administration of alumina gel as the binder of inorganic phosphate in their bodies. Although almost every patient receiving hemodialysis is treated by alumina gel-administration to reduce serum inorganic phosphate level, according to the recent studies, it has been elucidated that aluminum accumulates in the patient's brain due to the administered alumina gel and accordingly, the method of treatment by administration of alumina gel is extremely dangerous. As another method for treating hyperphosphatemia, administration of calcitonin has been tried. Although calcitonin's pharmacological function to reduce serum inorganic phosphate level is strong enough for 2 to 3 hours after its administration, since it is peptide hormone, persistency of its effectiveness is poor, and more over, since the state in the patient's body just after the administration of calcitonin differs drastically from the state when the calcitonin's effect has disappeared, the administration is apt to become a very hard treatment for the patient.

Still more, the administration of a peptide hormone derived from a foreign animal (for instance swine, eel and the like) gives an poorer effectiveness when continuously administered than the effectiveness when it was at the first time administered because of its antibody production, and there is a danger of anaphylaxis.

In addition, calcitonin's effectiveness can not be exhibited when orally administered, and accordingly, it is given by intramuscular injection and such a method of administration is accompanied by the patient's pain. Thus, it cannot be said that calcitonin is a safe pharmaceutic. In consideration of the above-mentioned fact, development of an agent safely usable for treating hyperphosphatemia has been demanded.

As a result of studying for finding a suitable compound among those substances which are endogenous within a healthy human body and high in safety, the present inventors have found that 24,25-$(OH)_2$-$D_3$ has an activity of reducing the inorganic phosphate level in serum, and based on the finding, they have attained the present invention.

It was found by the present inventors that administration of 24R,25-$(OH)_2$-$D_3$ to the rats in a state of hyperphosphatemia due to 5/6-nephrectomy (resulting in one third of one kidney remaining) caused the significant reduction of the inorganic phosphate level in the rat's serum. It was also found by the present inventors that administration of 24R,25-$(OH)_2$-$D_3$ to the Wistar rats to which puromycin-amino-nucleoside (produced by Sigma Co., hereinafter abbreviated and referred to as AN) had been administered to bring into the state of hyperphosphatemia caused the significant reduction of the inorganic phosphate level in their serum.

According to the above-mentioned findings, the present inventors administered 24R,25-$(OH)_2$-$D_3$ to a patient of chronic renal failure showing a symptom of hyperphosphatemia to find out that the inorganic phosphate level in the patient's serum was significantly reduced to the normal level of 2.5 to 5.5 mg/dl (concerning the normal level, refer to Wajima, T., "Clinical Chemical Analyses" Chapter V, Electrolytes, page 117, 1979, Ed. Tôkyo Kagaku Dojin).

In addition, it was found by the present inventors that administration of 24R,25-$(OH)_2$-$D_3$ to a patient of chronic renal failure who has been given hemodialysis with a dialyzing liquid containing 9 to 10 mg of calcium component/ml caused a significant reduction of the inorganic phosphate level in his serum to the normal level. In this connection, since the normal calcium level in human serum is 8.8 to 10.4 mg/dl, the concentration of calcium component in the dialysate is preferably 9 to 10 mg/dl. However, since it has been elucidated that the hemodialysis carried out frequently on one patient over a long period of time while using a dialysate of a concentration of calcium component of 9 to 10 mg/dl causes osteomalacia, 1-α-25-$(OH)_2$ or 1-α-$(OH)$-$D_3$ is used in recent years for preventing osteomalacia with a dialysate of a concentration of calcium component of 6 to 7.5 mg/dl. However, since the administration of 1-α-25-$(OH)_2$-$D_3$ or 1-α-$(OH)$-$D_3$ promotes not only the resorption of calcium but also the resorption of phosphorous from the bone or the absorption of calcium and phosphorous from intestinal tract to raise the inorganic phosphate level in serum, the above-mentioned alumina gel is used in combination.

In this connection, the present inventors have found that the use of a dialysate of a concentration of calcium component of 9 to 10 mg/dl with the administration of the antihyperphosphatemic agent of the present invention reduces the inorganic phosphate level in serum and improves the osteomalacia without causing metastatic calcification.

The activity of the present compound in controlling blood sugar level will be described as follows:

Although various injections and internal medicines have been developed for controlling the hyperglycemic state due to glycosuria to the normal level, such injections and internal medicines have various difficult problems, and the development of safer and more effective agent for controlling blood sugar level has been eagerly demanded. As a symptomatic agent against hyperglycemia, agents containing insulin-derivative of a form of injection and agents containing sulfonylurea-derivative of a form suitable for internal administration are commercialized.

As the insulin composition, other than the regular insulin which exhibits its effect immediately after administration, however, of which the effect does not maintains for a long period, there is the depot insulin composition to which various proteins are admixed to make the absorption into the patient's body slow and zinc is further bonded to reduce the solubility to the humor.

The agents for treating glycosuria in a form of internal medicine have shown a progress from sulfonyl urea-derivative to biguanide-derivative, and new type of sulfonylurea-derivative has appeared recently.

In recent years, through the long term epidemiological studies, presence of a correlation between the disturbance of smaller blood vessel of the patient of glycosuria and the extent of blood sugar control has gradually been ensured. Namely, it is to be expected that the strict maintenance of the normal blood sugar level will possibly prevent the progress of disturbance of smaller blood vessels. In the existing treatment of glycosuria by insulin, the amount of insulin to be administered at a time and the number of times of administration of insulin are adjusted so as to maintain the blood sugar level at hunger, and the daily level of urine sugar as normal as possible. However, since insulin is a peptide hormone, its life span in a living body is short and its action is strong, the fluctuation of the blood sugar level within a day of the patient of glycosuria is apt to be different from that of a healthy person, and it is extremely difficult to maintain the level within a normal range. Moreover, even if insulin is orally administered, its pharmacological effect can not be expected.

In consideration of the above-mentioned facts, development of a safe and stabilized agent for controlling blood sugar has been eagerly awaited.

As a result of studying on the endogeneous substances present in human body, of which safety has been varified, the present inventors have found that 24,25-$(OH)_2$-$D_3$ has an activity to regulate the human blood sugar level, and based on the finding, they have arrived at the present invention.

Namely, while using rats on which urine sugar was positively confirmed as a result of intraperitoneal administration of streptozotocin, and reduction of the urine sugar level and blood sugar level was shown as a result of administration of regular insulin and which showed a high urine sugar level and high blood sugar level again after a few days of the suspension of insulin-administration as model animal of glycosuria, the present inventors examined the endogeneous substances present in human body for finding a substance having an activity of regulating the blood sugar level within the rat body, and they have found that 24,25-$(OH)_2$-$D_3$ is active in blood sugar level control. The agent for blood sugar controlling according to the present invention exhibits the activity to reduce the blood sugar level by the oral administration of only a few micrograms per kg body weight, and in this sense, it is of a new type never seen hitherto. Moreover, in the case where the agent of the present invention was administered to patients suffering from glycosuria, significant reduction of the blood sugar level was observed. Namely, the agent for blood sugar controlling according to the present invention can exhibit its blood sugar controlling action even in human case.

In the next place, anti-tumour activity of the present compound will be described as follows:

The anti-tumour agent actually in use at present includes alkylating agents, metabolic-antagonist, antibiotics, plant alkaloids and immunotherapeutic agents and among them, many agents which show in vitro cytotoxic effect are also strong in their side effect.

As a result of examining the activity of the endogeneous substances present in living human body against tumour, the present inventors have found that 24,25-$(OH)_2$-$D_3$ shows in vivo as well as in vitro cytotoxic effect against various cancer cells and that even when it is administered over a long period it does not show any side effects.

Namely, in the present inventors' study for examining in vitro anti-tumor activity of 24,25-$(OH)_2$-$D_3$ against both K-562 cells derived from human leukemia and LICR-LON-HMy 2 cells derived from human myeloma, an action of inhibiting proliferation of these tumor cells or a cytotoxic activity against these tumor cells was recognized. Moreover, also in the experiments using mouse and rat as the host, anti-tumour effect of the compound was confirmed.

On the other hand, even after administering every day for 30 days 24,25-$(OH)_2$-$D_3$ in vivo at a daily dose rate of 1 mg/kg, any significant abnormal findings were not observed in the biochemical examination of the blood and the autopsy of the host animal. Moreover, in the observation of the appearance of the thus treated animals, the results of biochemical examination and the autopsy during and/or after 2 weeks of the single administration of 24,25-$(OH)_2$-$D_3$ at a dose rate of 150 mg/kg body weight, no abnormal findings were obtained. The present compound is an endogeneous substance and a safe anti-tumour agent of new type.

24,25-$(OH)_2$-$D_3$ has been also publicly known, for instance, it has been disclosed in Pharmacia (Japan), 10, 319–322, 1974. The chemical structural formulae of 24,25-$(OH)_2$-$D_3$ and its two optically isomeric molecules thereof are shown as follows:

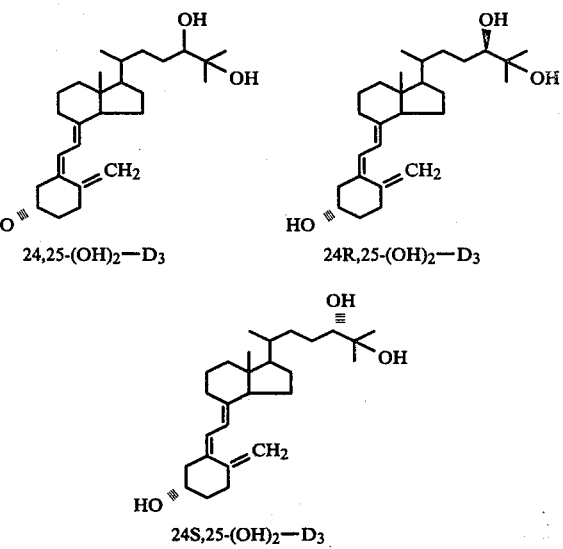

24,25-$(OH)_2$—$D_3$    24R,25-$(OH)_2$—$D_3$ 24S,25-$(OH)_2$—$D_3$ 24,25-$(OH)_2$-$D_3$ herein mentioned includes 24R,25-$(OH)_2$-$D_3$, 24S,25-$(OH)_2$-$D_3$ and their mixtures.

24R,25-$(OH)_2$-$D_3$ is particularly preferable.

The pharmaceutical composition according to the present invention contains the above-mentioned substance as the active ingredient, and is used in one of the various states mentioned below.

Although the pharmaceutical agent according to the present invention can be administered orally, parenterally or via rectal route, oral administration is preferable.

The pharmaceutical composition containing 24,25-$(OH)_2$-$D_3$ of the present invention as the active ingredient is used in one of the following states for administration, namely, tablet, powder, granule, suppository, capsule, alcoholic solution, such as ethyl alcohol, isopropyl alcohol, ethylene glycol and propylene glycol solution, oil solution, aqueous suspension, etc. As a solvent for oil solution, triglyceride ester of fatty acid such as capric acid and caprylic acid, corn oil, cotton seed oil, peanut oil, fish liver oil, oily esters, and the like are used. In addition, cacao butter and glycerol are desirable. Furthermore, as other components of the pharmaceutical composition, lactose, starch, talc, magnesium stearate, sorbic acid, sorbate salts, saccharides or their alcoholic derivatives, physiological saline solution, surfactants, antioxydants and the like are used in combination with the present compound.

The content of the present substance in the pharmaceutical composition is $2 \times 10^{-8}$ to $4 \times 10^{-1}$% by weight, preferably $2 \times 10^{-5}$ to $1 \times 10^{-1}$% by weight, the daily dose of the present compound to an adult patient (of average body weight of 50 to 60 kg) being $1 \times 10^{-2}$ to $1 \times 10^5$ micrograms, preferably $5 \times 10^{-1}$ to $1 \times 10^4$ micrograms.

The result of acute toxicological test of the present compound is as follows:

Acute oral mammalian toxicity 0.3 ml of ethanolic solution containing 150 mg of 24R,25-(OH)$_2$-D$_3$ was suspended in 15 ml of Panacete ® 810 (triglyceride ester of C$_8$ and C$_{10}$-fatty acid, made by Nippon Oil & Fats Co., Ltd.) to obtain a suspension containing 2% by weight of ethanol. The thus prepared composition was orally administered to a group of male mouse of ICR-strain consisting of 10 animals at a dose rate of 150 mg of 24R,25-(OH)$_2$-D$_3$ per kg. According to the observation for two weeks after administration, all the thus treated mice survived without any difference to those of control to which Panacete ® 810 containing 2% by weight of ethanol was orally administered.

Namely, since the test result showed that LD$_{50}$ (per os) of 24R,25-(OH)$_2$-D$_3$ to mouse was larger than 150 mg/kg, it can be said that 24R,25-(OH)$_2$-D$_3$ is extremely safe for administration to mammals.

The present invention will be concretely explained more in detail while referring to the following non-limitative examples.

For reference, the structural confirmation of optical isomers of 24R,25-(OH)$_2$-D$_3$ at 24-carbon was carried out while referring to Tetrahedron Letters, Vol. 26, 2203–2206, 1975.

EXAMPLE 1

To 16 subgroups of male Wistar rats of body weight of 150±40 g (one subgroup consisting of 5 rats), a solution of Vitamin D$_3$ dissolved in corn oil at 600 micrograms/ml was orally administered once a day for continuous 4 days at a daily dose rate of 0.5 ml/100 g body weight to prepare the rats artifically suffering from hypercalcemia. After one day's fasting from the final administration of Vitamin D$_3$, the calcium level in the serum of each rat of the first subgroup was on the average 13.5±0.4 mg/dl. The remaining 15 subgroups of the rats were divided into 3 groups each consisting of 5 subgroups and subjected to the following tests.

To the rats of the first group, a solution of 20 μg of 24R,25-(OH)$_2$-D$_3$ per ml of Panacete ® 810 was orally administered once at a dose rate of 100 micrograms of 24R,25-(OH)$_2$-D$_3$/kg body weight, and the rats were sacrificed one subgroup after another subgroup after 2, 5, 8, 12 and 24 hours of the administration to collect blood from vena cava inferior.

To the rats of the second group, a solution of porcine calcitonin in a physiological saline solution containing 4% by weight of gelatin was subcutaneously injected at a dose rate of 4 MRCU/kg body weight instead of the solution of 24R,25-(OH)$_2$-D$_3$ and they were treated as those of the first group.

To the rats of the third group, only the same triglyceride ester as in the first group was orally administered, and they are treated in the same manner as in the first group.

The calcium level of the respective sera of the thus collected blood was determined by OCPC method (Orthocresol Phthalein Complexone method) and shown in Table 1.

As seen in Table 1, one of the present compound, 24R,25-(OH)$_2$-D$_3$ reduced the calcium level which had been artificially raised by Vitamin D$_3$ to the normal level of 10.5±0.4 mg/dl, and maintained the reduced level for a long period of time of 12 hours. On the other hand, although porcine calcitonin once reduced the raised level of serum calcium concentration nearly to the normal level, its effect was not recognized after 2 hours of its administration and thereafter.

TABLE 1

| Group No. | Agent | Calcium level in serum (mg/dl) after hours of administration | | | | |
|---|---|---|---|---|---|---|
| | | 2 | 5 | 8 | 12 | 24 |
| 1 | 24R,25-(OH)$_2$—D$_2$ | 12.5 ± 0.4 | 11.0 ± 0.5 | 10.5 ± 0.5 | 10.5 ± 0.4 | 10.8 ± 0.3 |
| 2 | calcitonin | 10.8 ± 0.5 | 13.0 ± 0.4 | 13.4 ± 0.4 | 13.9 ± 0.5 | 13.4 ± 0.4 |
| 3 | control | 13.6 ± 0.3 | 13.8 ± 0.3 | 13.8 ± 0.4 | 14.1 ± 0.4 | 13.6 ± 0.5 |

EXAMPLE 2

Four subgroups of male Wistar-rats (a subgroup consisting of 5 animals) were used as the test animals, and they were fasted one whole day before the test.

To the rats of the first group consisting of 2 subgroups, a solution of 24R,25-(OH)$_2$-D$_3$ in the triglyceride ester used in Example 1 was orally administered once at a dose rate of 100 micrograms of the agent/kg body weight. After 2 and 5 hours of the administration, they were sacrificed to collect the blood specimen from vena cava inferior, which was subjected to analysis for calcium level in serum.

To the rats of the second group consisting of 2 subgroups, only the triglyceride used in Example 1 was administered orally, and while using them as control, the calcium level in their serum was determined as in the first group. The results are shown in Table 2.

As seen in Table 2, the calcium level did not show any change by any of the above-mentioned treatments.

TABLE 2

| Group No. | Agent | Calcium level in serum (mg/dl) after hours of administration | |
|---|---|---|---|
| | | 2 | 5 |
| 1 | 24R,25-(OH)$_2$—D$_3$ | 10.6 ± 0.3 | 10.5 ± 0.3 |
| 2 | control | 10.5 ± 0.4 | 10.5 ± 0.3 |

EXAMPLE 3

To 4 subgroups of male Wistar rats of 150±40 g of body weight (a subgroup consisting of 5 animals), parathyroid hormone (PTH, Sigma Bovine parathyroid TCA powder, 134 USPU/mg) dissolved in a physiological saline solution containing 4% by weight of gelatine was subcutaneously injected at a dose rate of 150 USPU/100 g body weight, the volume injected being 0.4 ml/100 g body weight to prepare the rats artificially suffering from hypercalcemia.

After one hour of the injection, an ethanolic solution of 24R,25-(OH)$_2$-D$_3$ was intraperitoneally administered to the rats of first group consisting of 2 subgroups at a dose rate of 50 micrograms of the agent per kg body weight, and they were sacrificed after 2 to 5 hours of the injection to collect the blood specimen from vena cava inferior.

The rats of the second group, after one hour of the administration of the parathroid hormone, were intraperitoneally administered only with ethanol, and treated as in the first group for taking the blood specimen.

The calcium level in serum obtained by OCPC method is shown in Table 3.

TABLE 3

| Group No. | Agent | Calcium level in serum (mg/dl) after | |
|---|---|---|---|
| | | 2 hours | 5 hours |
| 1 | 24R,25-(OH)$_2$—D$_3$ | 12.5 ± 0.5 | 10.5 ± 0.5 |
| 2 | Control | 13.4 ± 0.4 | 13.8 ± 0.4 |

As are seen in Table 3, 24R,25-(OH)$_2$-D$_3$ was effective in preventing the raise of calcium level in serum of the rats of artificial hypercalcemia due to PTH to the normal level.

EXAMPLE 4

In the present example, it is shown that 24R,25-(OH)$_2$-D$_3$ has a function of preventing the occurrence of hypercalcemia on rats administered with 1-α-hydroxycholecalciferol (hereinafter referred to as 1-α-(OH)-D$_3$).

Six subgroups of male Wistar rats of 130±30 g of body weight were subjected to the test while dividing the rats into 3 groups, each group consisting of 2 subgroups and each subgroup consisting of 5 animals. To the rats of the first group, after fasting for a night, an ethanolic solution of 1-α-(OH)-D$_3$ was intraperitoneally administered at a dose rate of 10 micrograms of 1-α-(OH)-D$_3$/kg body weight. To the rats of the second group, a solution of 24R,25-(OH)$_2$-D$_3$ in the triglyceride ester used in Example 1 was orally administered at a dose rate of 100 micrograms/kg body weight simultaneously with the same administration of 1-α-(OH)-D$_3$ as in the rats of the first group.

The third group of the rats was used for control only with the oral administration of the triglyceride ester used in Example 1. The rats of each group were successively sacrificed after 10 and 18 hours of the last administration to collect the blood specimen from vena cava inferior, which was analyzed for calcium level in serum according to OCPC method. The results of analysis are shown in Table 4.

TABLE 4

| Group No. | Agent | Calcium level (mg/dl) in serum after | |
|---|---|---|---|
| | | 10 hours | 18 hours |
| 1 | 1-α-(OH)—D$_3$ | 13.4 ± 0.6 | 14.5 ± 0.5 |
| 2 | 1-α-(OH)—D$_3$ and 24R,25-(OH)$_2$—D$_3$ (the present invention) | 11.5 ± 0.5 | 10.6 ± 0.4 |
| 3 | Control | 10.0 ± 0.3 | 10.1 ± 0.2 |

As seen in Table 4, while 1-α-(OH)-D$_3$ raised the calcium level in serum, 24R,25-(OH)$_2$-D$_3$ administered in combination with 1-α-(OH)-D$_3$ prevented the raise of the calcium level in serum.

EXAMPLE 5

After injecting 0.5 ml of ascites of Walker-carcinosarcoma 256 adjusted to contain 2×10$^6$ tumour cells per microliter into the upper part of the right thigh of a Sprague-Dawley rat of body weight of 90–140 g, a solution of 24R,25-(OH)$_2$-D$_3$ in the triglyceride ester used in Example 1 at a concentration of 0.5 microgram/100 microliter was orally administered once a day for continuous 7 days at a daily dose rate of 20 micrograms of 24R,25-(OH)$_2$-D$_3$ per kg body weight of the rat. Then the rat was sacrificed to collect the blood specimen from vena cava inferior. The blood specimen was also collected in the same manner from a rat of the same strain injected with the ascites in the same manner as in the first rat, however, only administered with the triglyceride ester. The two levels of calcium in the respective sera of the two groups were compared in Table 5.

TABLE 5

| Treated with | Calcium level in serum (mg/dl) | |
|---|---|---|
| | Before transplantation | After one week of transplantation |
| 24R,25-(OH)$_2$—D$_3$ | 10.5 ± 0.3 | 11.2 ± 0.6 |
| Control | 10.3 ± 0.4 | 18.6 ± 0.8 |

As are seen in Table 5, 24R,25-(OH)$_2$-D$_3$ prevented the raise of calcium level in serum of rat transplanted with the tumour cell.

EXAMPLE 6

Soft capsule composition was prepared by using a conventional capsule-forming machine and according to the conventional process from a solution of 5 mg of 24R,25-(OH)$_2$-D$_3$ in 1,000 g of triglyceride ester of fatty acid used in Example 1 additionally containing the following component for capsule-wall dissolved therein by warming, while adjusting to contain 0.5 microgram of 24R,25-(OH)$_2$-D$_3$ within each capsule.

Recipe for capsule-wall forming component:
10 parts by weight of gelatine,
4 parts by weight of glycerol,
0.1 part by weight of sorbic acid and
15 parts by weight of water In a similar manner, capsule compositions respectively containing one, two and five micrograms of the active ingredient were prepared.

The thus prepared capsule composition was tentatively applied to the following two cases of human hyperparathyroidism accompanied by hypercalcemia:

To a male patient of age of 40 suffering from hyperparathyroidism accompanied by hypercalcemia, one of the capsule composition prepared as above containing 1 microgram of the active ingredient in one capsule was orally administered at a daily dose of 10 micrograms of 24R,25-(OH)$_2$-D$_3$ for continuous 4 days.

The calcium level in the patient's serum showed a reduction from the level before administration of 13.8 mg/dl to the level after administration for 4 days of 10.8 mg/dl.

EXAMPLE 7

A man of age of 58 who was subjected to hemodialysis on account of renal failure and became hypercalcemia due to the four month administration of active Vitamin $D_3$ at a daily dose of 0.5 to 1.0 microgram was treated by the oral administration of the capsule composition similar to that prepared in Example 6 for three continuous days at a daily dose of 10 micrograms of $24R,25\text{-}(OH)_2\text{-}D_3$. The calcium level in the patient's serum was reduced from the value before the administration of 12.8 mg/dl to 10.5 mg/dl after the completion of the treatment.

EXAMPLE 8

To a female patient of age of 32 diagnosed to be sarcoidosis accompanied by hypercalcemia of the calcium level in her serum of 14.0 mg/dl, the capsule composition similar to that prepared in Example 6 was administered orally at a daily dose of two capsules each containing 5 micrograms of $24R,25\text{-}(OH)_2\text{-}D_3$ for continuous 5 days. The calcium level in serum from the blood specimen collected on the sixth day of the commencement of the treatment was 10.8 mg/dl.

EXAMPLE 9

Twenty male Wistar rats of average body weight of 250 g were divided equally into two groups, and used in the following test:

After 36 hour fasting, all the rats were subjected to pyloric ligation, and the rats of the first group were administered with 2 ml/kg of Panacete ®810 (triglyceride ester of $C_8$ and $C_{10}$-fatty acid, made by Nippon Oil & Fats Co., Ltd.) containing 0.2% by weight of ethanol intraperitoneally once just after ligation. The rats of the second group were administered with $24R,25\text{-}(OH)_2\text{-}D_3$ dissolved in Panacete ®810 containing 0.2% by weight of ethanol intraperitoneally at a dose rate of 200 micrograms/kg body weight once just after ligation. After 15 hours of administration, all the rats were subjected to gastrectomy, and the presence or absence of the gastroparietal ulcer was examined on all the resected stomach.

As a result, the occurrence of gastric ulcer was found on 9 rats of 10 rats of the first group, and on 2 rats of 10 rats of the second group. For reference, it has been in advance confirmed that Panacete ®810 does not affect the occurrence of the ulcer.

In a similar test, $24S,25\text{-}(OH)_2\text{-}D_3$ was used instead of $24R,25\text{-}(OH)_2\text{-}D_3$ to examine its effect in preventing the occurrence of gastric ulcer due to pyloric ligation. As a result, the occurrence of gastric ulcer was recognized on 3 rats of 10 rats of the group similarly treated to those of the second group.

EXAMPLE 10

Fourty five male rats of body weight of 240 to 260 g were equally divided into three groups, each consisting of 15 animals, and they were subjected to an operation following the method of Okabe et al. (refer to Amer. J. Dig. Dia., 16, 277, 1971), in which under anesthesia by ether, a circular frame made of a metal was placed on the serosa 5 to 7 mm from the pylorus and 0.06 ml of gracial acetic acid was poured onto the round part within the frame and after 30 sec, the acetic liquid was removed with the frame.

The thus operated rats of the first group were administered orally with a suspension of 100 ppm of $24R,25\text{-}(OH)_2\text{-}D_3$ in Panacete ®810 containing 0.2% by weight of ethanol once a day for continuous 10 days from the third day of the operation at a daily dose rate of 20 micrograms of $24R,25\text{-}(OH)_2\text{-}D_3$/kg. To the thus operated rats of the second group (control), only Panacete ®810 was orally administered at a daily dose rate of 2 ml/kg for continuous 10 days.

The thus operated rats of the third group were used in the comparative test. Namely, they were treated in the same manner as those of the first group except for administration of gefarnate (3,7-dimethyl-2,6-octadienyl-5,9,13-trimethyl-4,8,12-tetradecatrienoate) at a daily dose rate of 20 microgram/kg body weight in stead of $24R,25\text{-}(OH)_2\text{-}D_3$ in the first group.

After finishing the final administration, all the rats were sacrificed by ether and their duodenum was taken out for autopsy. The length and the width of the ulcer found on the duodenum were measured, and their product with a unit of $mm^2$ was taken and named as the ulcer coefficient. The rate of healing of the ulcer was calculated by the following formula:

$$\% \text{ Rate of ulcer healing} = \frac{C - U}{C} \times 100$$

wherein C is the ulcer coefficient of control and U is the ulcer coefficient of the group to which the present compound was administered.

The results of the test and the comparative test are summarized as follows:

(1) the rats (the first group) orally administered with 20 micrograms of $24R,25\text{-}(OH)_2\text{-}D_3$/kg every day for continuous 10 days showed the ulcer coefficient of 1.5 ($mm^2$) and the rate of ulcer healing of 80%, and on the other hand, (2) the rats (the third group) orally administered with 20 micrograms of gefarnate/kg every day for continuous 10 days showed the ulcer coefficient of 7.5 ($mm^2$) and the rate of ulcer healing of 0.

EXAMPLE 11

Effect of the present compound on the weight ratio of thymus to body, and the total number of nucleated thymic cells Thirty-two male JCL-Wistar rats in tenth week after birth were used in the present test while keeping them in a room at $21\pm1°$ C. and $60\pm5\%$ RH with solid diet (CE 2) and water taken ad lib.

They were divided equally into 4 groups (one group consisting of 8 animals), their treatments in the test being as follows:

First group:
    subcutaneous injection of aqueous physiological saline solution, at a daily dose rate of 1 ml/kg for continuous 12 days and oral administration of Panacete ® 810 (triglyceride ester of $C_8$ and $C_{10}$ fatty acid, made by Nippon Oil & Fats Co., Ltd.) at a daily dose rate of 1 ml/kg for continuous 12 days.

Second group:
    subcutaneous injection of puromycin aminonucleoside dissolved in aqueous physiological saline solution at a daily dose rate of 15 mg/kg, once a day for continuous 12 days and oral administration of Panacete as in the first group.

Third group:
    subcutaneous injection of puromycin aminonucleoside as in the second group and oral administration of $24R,25\text{-}(OH)_2\text{-}D_3$ dissolved in Panacete 810 once a day at a daily dose rate of 100 micrograms/kg for continuous 12 days.

Fourth group:

subcutaneous injection of puromycin aminonucleoside as in the second group and oral administration of 24S,25-(OH)$_2$-D$_3$ dissolved in Panacete 810 once a day at a daily dose rate of 100 micrograms/kg for continuous 12 days.

Then, just after blood-sampling from vena cava inferior, their thymus was resected and after removing the adhered adipose tissue thereto, the weight of the thymus was determined by microbalance.

After uniformly loosing the thymus in phosphate buffer solution with a forcets and fully pipetting, the mixture was filtered through a stainless steel mesh (Tylar standard #200) and the filtrate containing the thymic cells was stained with Türk's solution. The thus stained specimen was subjected to counting under a microscope. The results are shown in Table 6.

TABLE 6

| Group No. | Weight ratio: thymus/body | Number of thrymocytes |
|---|---|---|
| 1 | 0.00130 ± 0.00037 | (40 ± 6.5) × 10$^7$ |
| 2 | 0.00049 ± 0.000088 | (63 ± 1.0) × 10$^7$ |
| 3 (the present invention) | 0.00101 ± 0.00011 | (32 ± 5.5) × 10$^7$ |
| 4 (the present invention) | 0.00981 ± 0.000091 | (30 ± 4.5) × 10$^7$ |

EXAMPLE 12

After feeding the rats (the same number and the same grouping) of the same strain and treating them in the same manner as in Example 11, their thymus was resected, and an analysis of the pattern of the size of the thymic cells was carried out while using Fluorescence Activated Cell Sorter (FACS II, made by Becton-Dickinson Co.) as follows:

After loosing the resected thymus in phosphate buffer solution sufficiently with a pincette, pipetting well and passing the mixture through a standard #200 Tyler stainless steel mesh, the filtrate was treated with an aqueous 0.83% by weight ammonium chloride buffer solution containing tris-hydroxyaminomethane to carry out hemolysis of the erythrocytes intermingled therein followed by three times of washing with the phosphate buffer solution. After adjusting the concentration of the thus obtained thymic cell to 5×10$^6$ cells/ml with the addition of the phosphate buffer solution, the above-mentioned analysis was carried out. The ratio of the number of living thymic cells to the total number of the thus obtained thymic cells was confirmed to be higher than 95% after staining with trypan blue and counting under microscope.

The results of analysing the pattern of the size of the thymic cells are as follows:

In the group only administered with puromycin aminonucleoside (the second group), the number ratio of the cells a little larger than the normal cell to the total cells is larger than that of the control group (the first group), however, in the group administered with both puromycin aminonucleoside and 24R,25-(OH)$_2$-D$_3$ or 24S,25-(OH)$_2$-D$_3$ (the third group and the fourth group), the ratio was the same as that of the control group.

The results show that the present compound prevented the effect of puromycin aminonucleoside of enlarging the size of the thymic cells.

EXAMPLE 13

The effect of the present compound on the blastoid-transformation of rat lymphocytes in the peripheral blood was examined as follows:

After mixing each of the blood specimens taken from the respective rats of the four groups in Example 11 added with heparin and RPMI-1640 culture medium at a weight ratio of 1:1, the mixture was added to Ficoll-Paque solution, and the thus obtained mixture was subjected to centrifugal separation at 400 G for 20 min to collect the layer of mononucleates. After washing the thus collected mononucleates three times with PRMI-1640 culture medium (in a liquid state), the washed mononucleates were suspended into RPMI-1640 culture medium added with 10% by weight of calf serum to be in concentration of 1.5×10$^6$ cells/ml.

Hundred microliters of the thus prepared suspension was placed in the pit of Pharcon microtest II plate, and after adding a substance promoting cell division (hereinafter referred to as mitogen) and RPMI-1640 culture medium added with 10% by weight of calf serum to the thus placed suspension to make the total volume 200 microliters, the thus prepared mixture was incubated for 72 hours under a gas (a 95:5 by volume mixture of air and carbon dioxide saturated with moisture) flow at 37° C. $^3$H-methylthymidine of specific activity of 5 Ci/mmol was added to the mixture during incubation at the time 24 hours before the incubation was over in an amount corresponding to 0.5 micro Ci.

After the incubation was over, the cells in the culture were collected by filtering the cultured mixture, and the amount of radioactive isotope uptaken into the cells was determined by a liquid scintillation counter.

For reference, the mitogen used in the present test is concanavalin A for T-cell or lipopolysaccharide for B-cell.

The results of the present test are shown in Table 7.

TABLE 7

Effect of the present compound on blast-transformation of mononucleates shown by the uptake of $^3$H—methylthymidine ($^3$H—TdR) into the cell

| | | Uptake of $^3$H—TdR in the presence of a mitogen such as | |
|---|---|---|---|
| Origin of mononucleate | Number of mononucleate[1] | Concanavalin A (cpm)[2] | Lipopolysaccharide (cpm) |
| First group | 1.00 | 4503 ± 663 | 4327 ± 620 |
| Second group | 0.21 ± 0.13 | 2456 ± 191 | 1553 ± 633 |
| Third group (the present invention) | 0.68 ± 0.17 | 3995 ± 412 | 3568 ± 372 |
| Fourth group (the present invention) | 0.58 ± 0.15 | 3582 ± 362 | 3126 ± 351 |

Note:
[1] the ratio of the number of mononucleate of the blood taken from the rat of the first group to that from one of the respective groups (second, third and fourth), taking the number of mononucleate of the blood taken from the first group as 1.00.
[2] cpm = count/min

EXAMPLE 14

Effects of plasma derived from a patient suffering from chronic renal failure or uremia treated with the present compound or not treated therewith on blastoid-transformation of lymphocytes from a healthy person Heparinized fresh peripheral blood of a normal person was mixed with Ficoll-Paque solution, and after subjecting the mixture to ultracentrifugal separation, the layer of lymphocyte was collected, and after washing the layer three times with phosphate buffer solution, the washed lymphocytes were dispersed in suspension in RPMI-1640 culture medium (liquid) at a concentration of $6 \times 10^5$ cells/ml.

In the pits of Farcon microtest plate II provided with 96 round bottomed pits, 170 microliters of the thus prepared suspension of lymphocytes, 10 microliters of an aqueous solution of a mitogen (lectin from the seed of Phaseolus vulgaris or lipopolysaccharide) and 20 microliters of plasma taken from each one of eight patients suffering from chronic renal failure or uremia and having been treated by oral administration of 24R,25-(OH)$_2$-D$_3$ at a daily dose of 0.5 to 1.0 microgram of the compound with capsule composition prepared in Example 6 for 1 to 6 months continuously or each one of eight patients of the same disease, however, not having been treated with the compound were placed as a total volume of 200 microliters, and after incubating the object for 65 hours under the same conditions as in Example 12, a solution of $^3$H-methylthymidine ($^3$H-TdR) of 1 micro Ci (the solution containing 100 micro Ci of $^3$H-TdR in 1 ml) was added to the object, and the incubation was continued further for 10 hours. Then, the specimen was harvested to determine the uptake of $^3$H-TdR by the lymphocytes. In addition, the plasma of each patient was collected two times, namely, once before hemodialysis and once after hemodialysis, and accordingly the total patient system of the present test consists of two large groups one of which is administered and the other of which is not administered with the compound, and each large group consists of two groups one of which is not yet hemodialysed and the other of which has been already hemodialysed.

The results of the determination are shown in Table 8.

TABLE 8

| State of the patient at blood-gathering | | Uptake of $^3$H—TdR in the presence of | |
|---|---|---|---|
| 24R,25-(OH)$_2$—D$_3$ | Before or after hemodialysis | Lectin from kidney beans (cpm) | Lipopoly-saccharide (cpm) |
| Administered | before | 228906 ± 19081 | 158950 ± 48245 |
| | after | 222480 ± 21253 | 129984 ± 51385 |
| Not administered | before | 230096 ± 18268 | 164852 ± 41522 |
| | after | 105284 ± 17546 | 51229 ± 23845 |

Note: cpm = count/min

EXAMPLE 15

Forty male Wistar rats in 9th week after birth were divided into four groups, and the rats of each group were treated as follows.

To the rats of the first group were administered subcutaneously physiological saline solution once a day for continuous 12 days at a daily dose of 0.1 ml/100 g body weight with the simultaneous oral administration of triglyceride ester of fatty acid used in Example 1 (abbreviated as MCT) containing 0.1% by weight of ethanol once a day for continuous 12 days at a daily dose of 0.2 ml/100 g body weight followed by oral administration of only MCT once a day for another 3 continuous days at the same daily dose rate.

To the rats of the second group were subcutaneously administered a solution of 1.5 mg of puromycin aminonucleoside (abbreviated hereinafter as AN) in 0.1 ml of physiological saline solution once a day for continuous 12 days at a daily dose rate of 1.5 mg of AN/100 g body weight. The saline solution had been sterilized with a Milipore filter before administration. To the rats were further administered orally MCT in the same manner as in those of the first group.

To the rats of the third group were administered orally a solution of 1 microgram of 24R,25-(OH)$_2$-D$_3$ in 0.2 ml of MCT once a day for continuous 12 days at a daily dose rate of 1 microgram/100 g body weight with simultaneously subcutaneous administration of AN followed by oral administration of only MCT for another 3 days in the same manner as in the second group.

To the rats of the fourth group were administered orally a solution of 10 micrograms of 24R,25-(OH)$_2$-D$_3$ in 0.2 ml of MCT once a day for continuous 12 days at a daily dose rate of 10 microgram/100 g body weight with simultaneously with subcutaneous administration of AN followed by oral administration of only MCT for another 3 days in the same manner as in the second group.

On 15th day after the commencement of the abovementioned administration, blood specimen was collected from all the rats, and after preparing each specimen of serum from each blood specimen, the content of magnesium in each serum specimen was determined by atomic absorption method. The results of determination are shown in Table 9 as the average values of the respective groups.

TABLE 9

| | Content of magnesium in serum with the dose rates | | |
|---|---|---|---|
| Group of rats | AN$^{(1)}$ (mg/100 g b.w.) | 24R,25-(OH)$_2$—D$_3$$^{(2)}$ (mg/100 g b.w.) | Mg in serum (mg/dl) |
| 1st | 0 | 0 | 4.2 ± 0.25 |
| 2nd | 1.5 | 0 | 6.4 ± 0.38 |
| 3rd (the present invention) | 1.5 | 1 | 4.5 ± 0.32 |
| 4th (the present invention) | 1.5 | 10 | 4.3 ± 0.30 |

Notes:
$^{(1)}$dissolved in 0.1 ml of physiological saline solution/100 g body weight.
$^{(2)}$dissolved in 0.2 ml of MCT/100 g body weight.

As are seen in Table 9, since the content of magnesium in the serum of rats in the fourth group is not so much different from that in the serum of rats in the first group, it is considered that 24R,25-(OH)$_2$-D$_3$ is effective in preventing hypermagnesemia as well as improving nephrosis while taking the raise of magnesium content in the second group into account.

EXAMPLE 16

Forty male Wistar rats in 9th week after birth were divided equally into four groups, and the rats of each group were treated as follows:

The rats of the first group were raised with a normal diet (TD-81144) with daily oral administration of 0.2 ml of MCT (refer to Example 15)/100 g body weight for 5 weeks.

The rats of the second group were raised with a Vitamin D-deficient diet (TD-81143, made by TEKLAD Co., U.S.A., which causes abnormal metabolism of magnesium) with daily oral administration of 0.2 ml of MCT/100 g body weight for 5 weeks.

The rats of the third group were raised with the Vitamin D-deficient diet as in those of the first group with daily oral administration of 1 microgram of 24R,25-$(OH)_2$-$D_3$ dissolved in 0.2 ml of MCT/100 g body weight for 5 weeks.

The rats of the fourth group were raised with the Vitamin D-deficient diet as in those of the first group with daily oral administration of 10 micrograms of 24R,25-$(OH)_2$-$D_3$ dissolved in 0.2 ml of MCT/100 g body weight for 5 weeks.

After the final administration was over, all the rats were sacrificed to collect their bones and blood respectively.

Serum specimen was prepared by the ordinary method from the blood specimen, and the bones were washed to remove marrow, lyopholized at −20° C. for 3 days and pulverized in a mortar. After de-ashing 50 mg of the thus pulverized bone with 1 ml of 2 N aqueous hydrochloric solution at room temperature, the insoluble matter was removed by filtration, and the filtrate was subjected to atomic absorption method to find out the content of magnesium in the bone specimen. Magnesium content of the serum specimen was determined by atomic absorption method.

The results are shown in Table 10.

TABLE 10

Contents of magnesium in serum and bone with the diet and dose rates

| Group of rats | Diet | Dose rate of 24R,25-$(OH)_2$-$D_3$[1] (microgram 100 g) | Content of magnesium in Serum (mg/dl) | Content of magnesium in Bone (%) |
| --- | --- | --- | --- | --- |
| 1st | TD-81144 | 0 | 3.8 ± 0.4 | 0.423 ± 0.027 |
| 2nd | TD-81143 | 0 | 5.2 ± 0.3 | 0.490 ± 0.032 |
| 3rd[2] (the present invention) | TD-81143 | 1 | 4.0 ± 0.3 | 0.395 ± 0.021 |
| 4th[2] (the present invention) | TD-81143 | 10 | 3.6 ± 0.3 | 0.396 ± 0.016 |

Notes:
[1] in 0.2 ml/100 g body weight of MCT
[2] in the scope of the present invention As are seen in Table 10, the content of magnesium in serum and in bone of the fourth group is lower than that of the second group to which the present compound was not administered and is close to that of the first group raised with the normal diet. These results show that the present compound, 24R,25-$(OH)_2$-$D_3$ prevented the occurrence of hypermagnesemia, due to bring raised with vitamin D-deficient diet.

EXAMPLE 17

To the three patients of chronic renal failure showing the hypermagnesemic symptoms of nearly the same extent to each other, 24R,25-$(OH)_2$-$D_3$ was orally administered in a form of soft capsule composition prepared in Example 6 at a daily dose of 2 to 5 micrograms for continuous 10 days. Magnesium level in their serum was determined before and after the administration following the ordinary method. The results are shown in Table 11.

TABLE 11

Conditions of treatments on hypermagnesemia and magnesium level

| Patient | Age | Sex | Magnesium level in serum (mg/dl) before administration | Magnesium level in serum (mg/dl) after administration | Dose of 24R,25-$(OH)_2$—$D_3$ (microgram/day for days) |
| --- | --- | --- | --- | --- | --- |
| A | 45 | male | 4.2 | 2.0 | 5 × 10 |
| B | 48 | female | 4.0 | 2.1 | 2 × 10 |
| C | 40 | female | 4.3 | 1.9 | 5 × 10 |

EXAMPLE 18

Preparation of a pharmaceutical composition for oral administration comprising 24R,25-$(OH)_2$-$D_3$ and its application Ten milligrams of 24R,25-$(OH)_2$-$D_3$ was dissolved in 10 ml of isopropyl alcohol and one ml of the thus obtained solution was admixed into 1,000 ml of distilled water under agitation. The thus obtained solution has the concentration of isopropyl alcohol of 0.1% by weight and the concentration of 24R,25-$(OH)_2$-$D_3$ of 1 microgram/ml and was called as the composition for oral administration A (abbreviated and referred to as Composition A hereinafter). In a similar manner as the above, another composition for oral administration of the concentration of 24R,25-$(OH)_2$-$D_3$ of 0.1 microgram/ml and the concentration of isopropyl alcohol of 0.1% by weight was prepared, and referred to hereinafter as Composition B.

Thirty male Wistar rats of average body weight of 200±30 g were subjected to operation of 5/6—nephrectomy.

Ten male Wistar rats of the same average body weight were subjected to sham operation. After one month of the operation, the above-mentioned Composition A or Composition B was given to each group (one group consisting of 10 animals) of the rats 6 times a week for 9 weeks to be taken ad lib. The amount of 24R,25-$(OH)_2$-$D_3$ taken by each rat for a week was calculated from the total amount of water taken by the rats of the group, the total amount of water taken by the rats being actually measured week after week. After the test was over (duration of the test being 9 weeks), all the rats were sacrificed to collect their blood from vena cava inferior to determine the concentration of inorganic phosphate in the serum by Molybdenum blue method. The results are shown in Table 12.

TABLE 12

| Classification | Group (ten animals) | Composition for oral administration | Amount[1] of 24R,25-(OH)$_2$—D$_3$ daily administrated | Concentration of inorganic phosphorus in serum (mg/dl) |
|---|---|---|---|---|
| Present invention | 5/6-kidney resected rat | Composition A | 92 | 10.5 ± 1.3 |
| Present invention | as above | Composition B | 8 | 11.5 ± 1.4 |
| Comparative control | as above | aqueous 0.1% by weight solution of isopropyl alcohol[2] | 0 | 14.0 ± 1.3 |
| Control | rats subjected to operation without resection of kidney | same as above | 0 | 10.2 ± 1.4 |

Notes:
[1] mean of 10 animals, unit of microgram/kg body weight.
[2] while using distilled water

EXAMPLE 19

Puromycin aminonucleoside (hereinafter abbreviated as AN) was dissolved in physiological saline solution to be the concentration of 15 mg of AN/ml.

The thus prepared solution was subcutaneously administered to 16 male Wistar rats in 9th to 10th week after birth divided equally into 3 groups once a day for continuous 5 days at a daily dose rate of 15 mg/kg body weight, and the administration of AN was suspended for the next 2 weeks. This cycle of 5 days of administration followed by 2 weeks of suspension of administration was repeated 5 times, and from the commencement of the 4th cycle, drinking water was substituted by one of the compositions for oral administration prepared in Example 18, namely, Composition A or Composition B to be taken ad lib by each one of the three groups of the rats for 38 days therefrom. After 38 days all the rats were sacrificed to collect blood specimen from vena cava inferior, and the content of inorganic phosphorus in the serum specimen prepared from the blood specimen. The results are shown in Table 13. As control, a group consisting of 8 male Wistar rats was used without giving AN and with the oral administration of aqueous 0.1% by weight isopropyl alcohol solution taken ad lib during the same 38 days as above. As comparative example, another group consisting of 8 male Wistar rats was used with the same administration of AN as in the test groups and with the oral administration of aqueous 0.1% by weight isopropyl alcohol taken ad lib as in the control group.

EXAMPLE 20

Eight patients suffering from chronic renal failure and not being subjected to hemodialysis shown in Table 14 were treated by oral daily administration of 24R,25-(OH)$_2$-D$_3$ in a form of the soft capsule composition obtained in Example 6 at a daily dose of 2 to 10 micrograms for 8 weeks. The concentration of inorganic phosphate in the serum of each patient before the above-mentioned administration and that after completion of the above-mentioned administration for 8 weeks were determined by the Molybdenum Blue method, the results being shown in Table 14.

TABLE 14

| Patient | | | Daily amount of administration of 24R,25-(OH)$_2$5-(OH)$_2$—D$_3$ (microgram) | Concentration of inorganic phosphate (mg/dl) | |
|---|---|---|---|---|---|
| No. | Sex | Age | | Before[1] | After[2] |
| 1 | male | 58 | 10 | 7.2 | 5.5 |
| 2 | male | 43 | 6 | 6.3 | 4.7 |
| 3 | female | 38 | 4 | 5.9 | 4.7 |
| 4 | male | 62 | 8 | 6.5 | 4.9 |
| 5 | female | 28 | 6 | 6.6 | 5.3 |
| 6 | male | 36 | 4 | 5.8 | 3.8 |
| 7 | male | 48 | 2 | 5.5 | 3.7 |
| 8 | female | 46 | 6 | 6.1 | 4.2 |
| average | | | | 6.24 ± 0.53 | 4.60 ± 0.66 |

Note:
[1] Before administration
[2] After administration.

TABLE 13

| Classification | Group | Composition for oral administration | Daily amount of[1] 24R,25-(OH)$_2$5-(OH)$_2$—D$_3$ taken by rat (microgram/kg b.w.) | Content of inorganic phosphate in serum (mg/dl) |
|---|---|---|---|---|
| Present invention | AN administered | Composition A | 64 | 10.2 ± 1.4 |
| Present invention | AN administered | Composition B | 5.8 | 11.4 ± 1.2 |
| Comparative Example | AN administered | Aqueous 0.1% by weight isopropyl alcohol solution | 0 | 13.7 ± 1.2 |
| Control | AN not administered | Aqueous 0.1% by weight isopropyl alcohol solution | 0 | 10.1 ± 1.2 |

Note:
[1] averaged value of 8 rats of the group, obtained by the same method in Example 18.

EXAMPLE 21

Eight patients suffering from chronic renal failure under the treatment of hemodialysis two times a week while using a dialysate containing 9 to 10 mg/dl of calcium component were further treated by oral administration of 24R,25-$(OH)_2$-$D_3$ in a form of the soft capsule composition obtained in Example 6 at a daily dose of 2 to 10 micrograms for 6 weeks, and the concentration of inorganic phosphate in the serum of each patient before the commencement of the administration and that after completion of the administration were determined by Molybdenum Blue method.

The results are shown in Table 15.

According to the roentgenographic examination of all the patients, metastatic calcification was not recognized after completion of the administration, and according to the results of bone biopsy of one patient after completion of the administration, improvement of osteomalacia was confirmed.

TABLE 15

| Patient No. | Sex | Age | Daily amount of administration of 24R,25-$(OH)_2$-$D_3$ (microgram) | Concentration of inorganic phosphorus (mg/dl) Before | After (administration) |
|---|---|---|---|---|---|
| 1 | male | 61 | 8 | 7.2 | 4.9 |
| 2 | male | 48 | 6 | 6.7 | 4.7 |
| 3 | female | 42 | 10 | 8.0 | 5.2 |
| 4 | female | 52 | 4 | 5.8 | 4.2 |
| 5 | male | 38 | 8 | 7.1 | 5.3 |
| 6 | female | 50 | 6 | 6.3 | 3.5 |
| 7 | male | 33 | 2 | 5.8 | 3.5 |
| 8 | female | 36 | 6 | 6.1 | 3.6 |
| Average | — | — | | 6.63 ± 0.77 | 4.36 ± 0.76 |

EXAMPLE 22

Among the male Wistar rats in 6th week after birth to which 60 mg of streptozotocin/kg body weight was intraperitoneally administered, those in which positive urine sugar was confirmed after one week of the administration, reduction of both urine sugar and blood sugar was shown by the administration of regular insulin and a state of hyper urine sugar and hyper blood sugar was confirmed after a few days of the administration of regular insulin. The confirmed rats were used as the model animals of glycosuria in the following tests. As control, the male Wistar rats intraperitoneally administered with aqueous physiological saline solution instead of streptozotocin were used. These rats were fed with an ordinary solid diet (CE-2, prepared by Nippon Crea Co., Ltd.)

The model animals were divided into two groups each consisting of 12 animals, and to the rats of the first group (according to the present invention), 24R,25-$(OH)_2$-$D_3$ was forcibly administered p.o. in a state of solution in MCT (triglyceride of $C_8$ and $C_{10}$-fatty acid) containing 0.2% by weight of ethanol once a day, 5 to 6 times a week for continuous 4 weeks at a daily dose rate of 10 micrograms/kg body weight. To the rats of the second group, only the same amount of MCT containing 0.2% by weight of ethanol as above was forcibly p.o. administered in the same manner as in the first group. To the rats of control, MCT containing 0.2% by weight of ethanol was forcibly p.o. administered in the same manner as in the second group.

After completing the administration, all the rats were fasted for 24 hours and then sacrificed to collect their blood specimen from vena cava inferior into a test tube containing EDTA and sodium fluoride, and the thus adjusted blood was analyzed for blood sugar by the enzyme method, the results being shown in Table 16.

TABLE 16

| Classification | Group of rats | Orally administered substance | Daily amount of 24R, 25-$(OH)_2$—$D_3$ administered (microgram/kg) | Blood sugar (mg/dl) |
|---|---|---|---|---|
| Present invention | treated by streptozotocin i.p. | 24R,25-$(OH)_2$—$D_3$ and MCT containing 2% by weight of ethanol | 10 | 208 ± 42 |
| Comparative test | treated by streptozotocin i.p. | MCT containing 2% by weight of ethanol | 0 | 310 ± 63 |
| Control | treated by aqueous physiological saline solution i.p. | MCT containing 2% by weight of ethanol | 0 | 90 ± 15 |

EXAMPLE 23

Three patients shown in Table 17 were treated by oral administration of a daily dose of 4 to 6 micrograms of 24R,25-$(OH)_2$-$D_3$ in a form of the soft capsule composition obtained in Example 6 for 3 continuous weeks. After the completion of administration, the patient was fasted for a night and their blood specimen was collected at 11:00 a.m. in the next morning. Blood sugar in the specimen was determined by the enzymatic method, the results of determination being shown in Table 17.

TABLE 17

| Patient Sex | Age | Daily administered amount[1] of 24R,25-$(OH)_2$—$D_3$ | Blood sugar level[2] before administration | Blood sugar level[2] after administration | Effectiveness[3] in reducing blood sugar level |
|---|---|---|---|---|---|
| Male | 49 | 4 | 168 | 120 | 100(%) |
| Male | 55 | 6 | 195 | 138 | 76 |
| Female | 60 | 6 | 183 | 131 | 82.5 |

TABLE 17-continued

| Patient | | Daily adminis-[1] tered amount of 24R,25-(OH)$_2$—D$_3$ | Blood sugar level[2] | | Effectiveness[3] in reducing blood sugar level |
|---|---|---|---|---|---|
| Sex | Age | | before administration | after administration | |
| Average | — | — | 182 ± 13.5 | 129.7 ± 9.1 | 86.2 |

Note:
[1]unit: microgram
[2]unit: mg/dl
[3]refer of Yoshida, Japanese J. Clin. Med., 24, 1470 (1966) Effectiveness of reducing blood sugar level (ERBS) is calculated from the following formula:

$$ERBS\ (\%) = \frac{LBA - LAA}{LBA - 120} \times 100,$$

wherein LBA is blood sugar level before administration of the composition according to the present invention, and LAA is blood sugar level after completing the administration of the composition according to the present invention, both being expressed by mg/dl.

EXAMPLE 24

Cultured K-562 tumour cell derived from human leukemia, which proliferates in a suspended state in RPMI-1640 culture medium added with 10% by weight of fetal bovine serum was used in the following experiment.

The cells were cultured in the above-mentioned culture medium at an initial cell concentration of $1 \times 10^5$ cells/ml with or without adding 24R,25-(OH)$_2$-D$_3$, which was placed in dishes kept in an incubator of an atmosphere consisting of 95% by volume of air and 5% by volume of gaseous carbon dioxide at 37° C. After culturing 3 days, the cultured medium was stained with tripan blue to count the total number of living cells. The results are shown in Table 18 with the specifically added substances into the culture medium other than fetal bovine serum of 10% by weight.

TABLE 18

| Classification | Specifically added substance[1] into culture medium (and its amount) | Number of K-562 cells after culture ($\times 10^5$ cells/ml) | Inhibition Rate of K-562 cells[2] (%) |
|---|---|---|---|
| Present invention | 24R,25-(OH)$_2$—D$_3$ 1 microgram/ml | 8.5 | 14 |
| Present invention | same as above 10 micrograms/ml | 3.5 | 65 |
| Comparative test | dimethylsulfoxide 5 milligrams/ml | 9.9 | 0 (standard) |
| Control | Nothing | 8.8 | — |

Note:
[1]once dissolved in dimethylsulfoxide in concentration of 5% by volume and the solution was added to the culture medium.
[2]calculated from the comparison of the proliferated number of the cells in the medium added wtih dimethylsulfoxide as the base.

As are seen in Table 18, 24R,25-(OH)$_2$-D$_3$ inhibited the proliferation of the tumour cell (K-562 leukemia cell) at the extent of 65% at a concentration of 10 micrograms/ml.

EXAMPLE 25

In a similar manner to Example 24, in vitro proliferated strain of LICR-LON-HMy 2 cells derived from human myeloma were cultured in each one of the same culture mediums as those used in Example 24. After culturing for 3 days, the cultured medium was stained with tripan blue and observed under a microscope to count the number of living cells, the results being shown in Table 19.

TABLE 19

| Classification | Specifically added substance[1] | Number of myeloma cells after culture $\times 10^5$ cells/ml) | Inhibition Rate of the myeloma cells (%) |
|---|---|---|---|
| Present invention | 24R,25-(OH)$_2$—D$_3$ 1 microgram/ml | 8.0 | 12 |
| Present invention | 24R,25-(OH)$_2$—D$_3$ 10 micrograms/ml | 0.4 | 96 |
| Comparative test | dimethylsulfoxide 5 milligrams/ml | 9.1 | 0 (standard) |
| Control | Nothing | 8.5 | — |

Note:
[1]refer to the note under Table 18.

In Table 19, the inhibition rate is based on the number of cells in the culture medium added specifically with dimethylsulfoxide as in Example 24.

As are seen in Table 2, 24R,25-(OH)$_2$-D$_3$ showed an inhibition rate of 96% on the proliferation of the tumour cell at its concentration of 10 micrograms/ml.

EXAMPLE 26

24R,25-(OH)$_2$-D$_3$ was dissolved in Panacete ® 810 containing 1% by weight of ethanol, and the solution was forcibly p.o. administered once a day for 30 continuous days to each male or female ICR mouse of the groups shown in Table 20 at each one of the daily dose rates also shown in Table 20.

As the control, Panacete 810 was solely and forcibly p.o. administered to the mice of the same strain once a day for 30 continuous days.

The state of these mice during the administration period was observed with the weighing of their body weight every day.

The results are shown in Tables 20-22.

TABLE 20

| Mouse | | Daily administered amount (microgram/kg. b.w.) | Hematological examination[1] | | | |
|---|---|---|---|---|---|---|
| Sex | Group | | RBC | WBC | Hemo. | Hema. |
| male | I | 10 | → | → | → | → |
| | II | 100 | → | → | → | → |
| | III | 1000 | → | → | → | → |
| female | IV | 10 | → | → | → | → |
| | V | 100 | → | → | → | → |
| | VI | 1000 | → | → | → | → |

Note:
[1]RBC: ethythrocyte count
WBC: leukocyte count
Hemo.: amount of hemoglobin
Hema.: hematcrit %
→: means the value was not different significantly from the value in control In addition, according to the body weight curve prepared from the determined body weight of the mice, no significant difference of body weight was observed among the groups, and between each group and the control group.

and caecum, eye-balls, submaxillary gland, urinary bladder, skin on the back, muscles, sternum, sternal marrow, femur and femural marrow.

What is claimed is:

TABLE 21

| Mouse | | Daily administered amount | Serum biochemical examination | | | | | | | | | | | | | |
|---|---|---|---|---|---|---|---|---|---|---|---|---|---|---|---|---|
| Sex | Group | (microgram/kg) | GOT | GPT | LDH | Ca | I-P | ALP | T-P | A/G | Alb. | T-Bil | Glu. | T-CHO | (1) |
| male | I | 10 | → | → | → | → | → | → | → | → | → | → | → | → | → |
|  | II | 100 | → | → | → | → | → | → | → | → | → | → | → | → | → |
|  | III | 1000 | → | → | ↓ | → | → | → | → | → | → | ↓ | ↓ | → | ↓ |
| female | IV | 10 | → | → | → | → | → | → | → | → | → | → | → | → | → |
|  | V | 100 | → | → | → | → | → | → | → | → | → | → | → | → | → |
|  | VI | 1000 | → | → | → | → | → | → | → | → | → | → | → | → | → |

Note:
(1) ↓ shows that the value is smaller than the value of the control.

TABLE 22

| Mouse | | Daily administered amount | Urine examination | | | | | |
|---|---|---|---|---|---|---|---|---|
| Sex | Group | (microgram/kg) | pH | sugar | protein | occultblood | ketone bodies | urobilinogen |
| male | I | 10 | → | → | → | → | → | → |
|  | II | 100 | → | → | → | → | → | → |
|  | III | 1000 | → | → | → | → | → | → |
| female | IV | 10 | → | → | → | → | → | → |
|  | V | 100 | → | → | → | → | → | → |
|  | VI | 1000 | → | → | → | → | → | → |

Furthermore, after resecting the various internal organs of all the mice and weighing each of the organs, it was found that the respective weights of the following internal organs of the mice of every group were not significantly different from those of the corresponding internal organs of the mice of control group: the organs being brain, pituitary, heart, lung, liver, spleen, kidney, adrenal, thymus, testes or ovary and uterus.

In addition, the following organs were fixed by aqueous 10% by weight formaldehyde solution after resecting, and were dyed with hematoxylin-eosin to carry out histopathological examination, however, no abnormal findings were obtained on these organs: brain, heart, lungs, kidneys, adrenal, liver, spleen, thyroid, pituitary, thymus, mesenteric limph nodes, testes or ovary and uterus, stomach, small intestine including jejunum, ileum and duodenum, large intestine including colon 1. A method for treating hypercalcemia, ulcer, reduced immune function, metabolic abnormality on magnesium, hyperphosphatemia, abnormality on blood sugar or tumour, which comprises administering to a human or an animal suffering therefrom a therapeutically effective amount of a compound selected from the group consisting of 24R,25-dihydroxycholecalciferol, 24S,25-dihydroxycholecalciferol and a mixtures thereof.

2. The method according to claim 1, wherein the compound is 24R,25-dihydroxycholecalciferol.

3. The method according to claim 1, wherein the compound is administered in oral dosage unit form.

4. The method according to claim 1, wherein the compound is administered in intraveneous dosage unit form.

* * * * *

UNITED STATES PATENT AND TRADEMARK OFFICE
CERTIFICATE OF CORRECTION

PATENT NO. : 4,442,093
DATED : April 10, 1984
INVENTOR(S) : Maeda et al.

It is certified that error appears in the above-identified patent and that said Letters Patent is hereby corrected as shown below:

On the cover page, in the column "Foreign Application Priority Data"; please amend the serial numbers "54-62688", "54-65869" and "54-70682" to read --57-62868--, --57-65689-- and --57-70682--.

Signed and Sealed this

Twenty-fifth Day of September 1984

[SEAL]

Attest:

GERALD J. MOSSINGHOFF

Attesting Officer

Commissioner of Patents and Trademarks